US007309795B2

(12) United States Patent
Turin

(10) Patent No.: US 7,309,795 B2
(45) Date of Patent: Dec. 18, 2007

(54) CITRAL DERIVATIVES

(76) Inventor: Luca Turin, 119 Albert Street, London (GB)

( * ) Notice: Subject to any disclaimer, the term of this patent is extended or adjusted under 35 U.S.C. 154(b) by 104 days.

(21) Appl. No.: 10/869,626

(22) Filed: Jun. 16, 2004

(65) Prior Publication Data
US 2005/0042242 A1 Feb. 24, 2005

Related U.S. Application Data

(63) Continuation of application No. PCT/US02/26446, filed on Aug. 20, 2002.

(60) Provisional application No. 60/377,914, filed on May 3, 2002, provisional application No. 60/389,298, filed on Jun. 17, 2002, provisional application No. 60/355,052, filed on Feb. 7, 2002, provisional application No. 60/342,150, filed on Dec. 19, 2001, provisional application No. 60/348,580, filed on Jan. 15, 2002.

(51) Int. Cl.
*C07D 331/02* (2006.01)
(52) U.S. Cl. .................................................. 549/90
(58) Field of Classification Search ................ 549/90
See application file for complete search history.

(56) References Cited

U.S. PATENT DOCUMENTS

| 3,549,624 A | 12/1970 | Conover et al. |
| 3,770,836 A | 11/1973 | Comes |
| 3,950,429 A | 4/1976 | Lamparsky et al. |
| 4,097,531 A | 6/1978 | Bledsoe, Jr. et al. |
| 4,151,103 A | 4/1979 | Evers et al. |
| 4,435,428 A | 3/1984 | Boden et al. |
| 4,521,331 A | 6/1985 | Martel et al. |
| 4,536,583 A | 8/1985 | Mookherjee et al. |
| 4,658,067 A | 4/1987 | Pittet et al. |
| 6,051,548 A | 4/2000 | Boden et al. |

FOREIGN PATENT DOCUMENTS

| DE | 26 17 816 A | 11/1977 |
| DE | 2617816 A | 11/1977 |
| EP | 0 219 146 A | 4/1987 |
| EP | 0 418 680 A | 3/1991 |
| EP | 0 801 049 A | 10/1997 |
| EP | 0 801 049 A2 | 10/1997 |
| FR | 1.393.451 | 2/1965 |
| FR | 1 393 451 | 2/1965 |
| FR | 1393451 A | 2/1965 |
| FR | 2 543 134 A | 2/1984 |
| FR | 2 543 134 | 9/1984 |
| GB | 1061732 A1 | 3/1967 |
| GB | 1 082 364 A | 9/1967 |
| GB | 1082364 A | 9/1967 |
| GB | 0 219 146 | 4/1987 |
| GB | 0 418 680 | 3/1991 |
| GB | 0 801 049 | 10/1997 |
| WO | WO 01/06853 | 2/2001 |
| WO | WO 01/06853 A | 2/2001 |
| WO | WO 2001/006853 A2 | 2/2001 |
| WO | WO 03/053901 | 7/2003 |
| WO | WO 03/053902 | 7/2003 |

OTHER PUBLICATIONS

Masaki Y et al., "Substrate-specific rearrangement and acetonidation of epoxy-ethers catalyzed by tetracyanoethylene", Chemistry Letters, No. 1, Jan. 1993, pp. 17-20, XP002224829.

Armstrong A et al., "Intramolecular Epoxidation in Unsaturated Ketones and Oxaziridines", Journal of the Chemical Society, Perkin Transactions 1, No. 21, Nov. 1, 2001, pp. 2861-2873, XP002224830.

Schulte-Elte K H et al., "Photooxygenation of 3,3-dialkylsubstituted allyl alcohols, Occurrence of syn preference in the ene addition of $^1O_2$ at E/Z isomeric allyl alcohols", Helvetica Chimica Acta, vol. 62 No. 3, Apr. 20, 1979, pp. 816-829, XP002224831.

Scheller M E et al., "Syntheses of Cyclopropyl Silyl Ketones", Helvetica Chimica Acta, vol. 68, No. 1, Feb. 5, 1986, pp. 44-52, XP002224832.

Rickards R W et al., "Synthesis of Four Stereoisomers of the Higher Dipteran Juvenile Hormone III Bisepoxide", Tetrahedron Letters, vol. 33, No. 52, Dec. 22, 1992, pp. 8137-8140, XP002224833.

Calo V et al., "Enantiomeric Selection via 1,3-Elimination. A Simultaneous Kinetic Resolution of Halohydrins and Epoxides", Tetrahedron Letters, vol. 49, 1978, pp. 4963-4966, XP002224834.

(Continued)

*Primary Examiner*—Bernard Dentz
(74) *Attorney, Agent, or Firm*—Miles & Stockbridge P.C.

(57) ABSTRACT

Improved citral derivatives, and fragrances and flavorings including the derivatives, that have a longer useful shelf life than citral and/or fragrances and flavorings including citral, are disclosed. In particular, the derivatives maintain the fragrance characteristics of citral, while lowering the allergic properties, and lemony flavors and fragrances with a longer shelf-life than citral, are disclosed. Also disclosed are methods of making the derivatives, and articles of manufacture including the derivatives. In one embodiment, the derivatives are prepared by replacing one or more double bonds in citral with a cyclopropyl group, which can be unsubstituted, or substituted with one or two lower alkyl, preferably methyl groups. The alkyl groups can optionally be substituted, for example, with electron donating groups, electron with drawing groups, groups which increase the hydrophilicity or hydrophobocity, and the like. In another embodiment, the derivatives are prepared by replacing the aldehyde group in citral with a nitrile, methyl ether or acetal group. The acetal groups can provide the compounds with a long lasting flavor or fragrance, where the acetals slowly hydrolyze to provide the aldehyde group in citral. In some embodiments, both the aldehyde and at least one of the double bond functional groups are both derivatized as described herein. Examples of suitable articles of manufacture include candles, air fresheners, perfumes, disinfectant compositions, hypochlorite (bleach) compositions, beverages such as beer and soda, denture cleanser tablets and flavored orally-delivered products such as lozenges, candies, and the like.

6 Claims, No Drawings

OTHER PUBLICATIONS

Ziegler F E et al., "Carbon-Carbon Bond Forming Reactions with Oxiranyl Radicals", Tetrahedron Letters, vol. 37, No. 35, Aug. 26, 1996, pp. 6299-6302, XP004030674.
Mori N et al., "Synthesis of (2R, 3R)-Epoxyneral, a Sex Pheromone of the Acarid Mite, Caloglyphus sp. (Astigmata: Acaridae)", Tetrahedron Letters, vol. 36, No. 9, Feb. 27, 1995, pp. 1477-1478, XP004028605.
Sakaguchi S et al., "Selective Oxidation of Monoterpenes with Hydrogen Peroxide Catalyzed by Peroxotungstophosphate (PCWP)", Journal of Organic Chemistry, vol. 61, No. 16, Aug. 9, 1996, pp. 5307-5311, XP002224835.
R. Jorritsma et al., "The chemistry of small ring compounds. Part 44[1]. Solvolysis of cyclopropyl sulfides and ethers", Recueil, Journal of the Royal Netherlands Chemical Society, 100/5, May 1981, p. 194-200.
T. Shirafuji et al., "The Reduction of gem-Dibromocyclopropanes by Means or Chromium (II) Acetate or Potassium Pentacyanocobaltate", Bulletin of the Chemical Society of Japan, vol. 44, No. 1, Nov. 1971, p. 3161-3164.
P. Grieco et al., "Construction of the gem-Dimethylcyclopropane Unit Employing Triphenylphosphonoium Isopropylide", Tetrahedron Letters No. 36, 1972, p. 3781-3783. Pergamon Press. Printed in Great Britain.
D. Seebach et al., "Ringöffnung von Cyclopropanon-bis-methylthio-acetalen Zu Ketonen und Dimethyldisulfid in Trifluoressigsäure . . . ", Tetrahedron Letters No. 36, 1973, pp. 3509-3512. Perfamon Press. Printed in Great Britain.
M. Julia et al., "No. 309.—Transposition homoallylique avec participation . . . ", Bulletin de la Société Chimique de France 1970 No. 5, p. 1805-1815.
M. Julia et al., "No. 311.—Transposition homoallylique avec participation . . . ", Bulletin de la Société Chimique de France 1970 No. 5, p. 1822-1833.
Abstract: Beilstein Registry No. 2087248, Copyright 1988-2003 Beilstein Institut zue Foerderung der Chemischen Wissenschaften.
Abstract: Beilstein Registry No. 2085216, Copyright 1988-2003 Beilstein Institut zue Foerderung der Chemischen Wissenschaften.
Weyerstahl P et al.: "Olfactory properties and convenient synthesis of furans and thiophenes related to rose furan and perillene and their isomers" Liebigs Annalen: Organic and Bioorganic Chemistry, vol. 10, Oct. 1, 1995 pp. 1849-1853, XP000608611.
Database Crossfire Beilstein Beilstein Institut zur Forderung der Chemischen Wissenschaften, Frankfurt am Main, DE; XP002233853.
Gagniant P et al: "Recherche dans la serie thiophenique. -1.-Etude de quelques acides omega.2-thienylaliphatiques de formule generate: C4H3S.(CH2)n.COOH" Bulletin De La Societe Chimique De France, 1948, pp. 1083-1087, XP002233849.
Tamaru Y et al: "The palladium catalyzed thienylation of allylic alcohols with 2- and 3-bromothiophenes and their derivatives" TETRAHEDRON, vol. 35, No. 3, 1979, pp. 329-340, XP002233850.
Arena G et al.: "Thermodynamics of protonation of some five-membered herteroaryl-carboxylates, -Alkannoates and—Trans-Propenoates", Journal of the Chemical Society, Perkin Transations 2, No. 10, Oct. 1993 pp. 1941-1945-XP002233851.
Garrigues B et al: "Synthese de 2-tert-butylthiophenes substitutes en position 5" Bulletin De La Societe Chimique De France, vol. 130, No. 1, 1993, pp. 58-63, XP002233852.
Rabinowitz M H et al: "Design of selective and soluble inhibitors of tumor necrosis factor—alpha converting enzyme (TACE)" Journal of Medicinal Chemistry, vol. 44, No. 24, Nov. 22, 2001, pp. 4252-4267, XP002266978.
Tashtoush H I et al: "Free radical coupling of alkyl and aryl halides with electron-deficient alkenes mediated by chromium(II) complexes" Chemische Berichte, vol. 126, No. 7, Jul. 2, 1993, pp. 1759-1761.
Masaki Y et al: "Substrate-specific rearrangement and acetonidation of epoxy-ethers catalyzed by tetracyanoethylene" Chemistry Letters, No. 1, Jan. 1993, pp. 17-20, XP002224829 the whole article, particularly p. 18, table 1, compound 1c4.

Armstrong A et al: "Intramolecular epoxidation in unsaturated ketones and oxaziridines" Journal of the Chemical Society, Perkin Transactions 1, No. 21, Nov. 1, 2001, pp. 2861-2873, XP002224830 the whole document, particularly p. 2862, scheme 4, compound 15c.
Schulte-Elte K H et al: Photooxygenation of 3,3-dialkylsubstituted allyl alcohols. Occurence of syn preference in the ene addition of (1)02 at E/Z-isomeric allyl alcohols Helvetica Chimica Acta, vol. 62, No. 3, Apr. 20, 1979, pp. 816-829, XP002224831 the whole document, particularly p. 819, table 2, compound 30.
Scheller M E al: "Syntheses of cyclopropyl silyl ketones" Helvetica Chimica Acta, vol. 68, No. 1, Feb. 5, 1986, pp. 44-52, XP002224832 the whole document, particularly p. 45, scheme 1, compound 8.
Rickards R. W. et al, Synthesis of four higher dipteran bisepoxide stereoisomers of the juvenile hormone III Tetrahedron Letters, vo 1, 33, No. 52, Dec. 22, 1992, pp. 8137-8140, XP002224833 the whole document, particularly p. 8139, scheme 2, compound 12.
Calo V et al: >>Enantiomeric selection via 1,3-elimination. A simultaneous kinetic resolution of halohydrins and epoxides>> Tetrahedron Letters, No. 49, 1978, pp. 4963-4966, XP002224834 the whole document, particularly p. 4963, compound (IX).
Ziegler Feet al: >>Carbon-Carbon Bond Forming Reactions with Oxiranyl Radicals>> Tetrahedron Letters, vol. 37, No. 35, Aug. 26, 1996, pp. 6299-6302, XP004030674 the whole document, particularly p. 6299, scheme 1, intermediate in the oxidation of 4 to 5.
Mori N et al: >>Synthesis of (2R, 3R)-Epoxyneral, a sex pheromone of the acarid mite, Caloglyphus sp. (Astigmata: Acaridae)>> Tetrahedron Letters, vol. 36, No. 9, Feb. 27, 1995, pp. 1477-1478,XP004028605 * the whole document.
Sakaguchi S et al: Selective oxidation of monoterpenes with hydrogen peroxidecatalyzed by peroxotungstophosphate (PCWP) Journal of Organic Chemistry, vol. 61, No. 16, Aug. 9, 1996 pp. 5307-5311, XP002224835—the entire document, particularly p. 5308, compounds 5a and 6a.
Filliatre C et al: "Synth~se de dArivAs cyclopropaniques en sArie p-menthAnique" Comptes Rendus Hebdomada1 Res Des Seances De L'Academie Des Sciences, Serie C, vol. 273, Oct. 18, 1971, pp. 1001-1004, XP002225027—the whole document.
Julia M et al: "PrAparation de composAs terpAniques et apparentAs, a partir de mAthyl cyclopropyl cAtone" Bulletin De La Societe Chimique De France, 1960, pp. 1072-1079, XP002225028 the whole document, particularly p. 1074, compounds (V), (VII) and (IX).
Taber D F et al: "Synthesis of (−)-delobanone" Journal of Organic Chemistry, vol. 66, No. 10, May 8, 2001, pp. 3423-3426, XP001233803 * the whole document.
Uenishi J et al: "An extremely mild desulfurization of thiiranes; an efficient transformation from geraniol to (+)- and (−)-linalool" Tetrahedron Letters, vol. 35, No. 36, 1994, pp. 6697-6700, XP001233804 * the whole document.
Taber et al., "Synthesis of (−)-Delobanone", Journal of Organic Chemistry, vol. 66 (2001) pp. 3423-3426—see schemes 1 and 2, compound 9.
Uenishi et al., "An extremely mild desulfurisation of thiiranes; An efficient transformation from geraniol to (+)- and (−)-linalool", Tetrahedron Letters, vol. 35 (1994) No. 36, pp. 6697-6700—see scheme 2, table 1.
Scheller M. E. et al.: "Photochemical reactions. Photochemistry of acylsilanes: photolysis and thermolysis of cyclopropyl silyl ketones" Helvetica Chimica Acta, vol. 73, No. 4, Jun. 20, 1990, pp. 922-931.
Database XFire, Beilstein Registry No. 6383807.
Database XFire, Beilstein Registry No. 2087248.
Keiji Maruoka, Yoshimi Fukutani, Hisashi Yamamoto, Communications, "Trialkylaluminum-Alkylidene Iodide. A Powerful Cyclopropanation Agent with Unique Selectivity", Journal of Organic Chemistry, vol. 50, No. 22, 1985, pp. 4412-4414.
Gary A. Molander and Lori S. Harring, Articles, "Samarium-Promoted Cyclopropanation of Allylic Alcohols", Journal of Organic Chemistry, vol. 54, No. 15, 1989, pp. 3525-3532.
Andreja Čercek, Branko Stanovnik, Anton Štimac, and Miha Tisler "1, 3-Dipolar Cycloaddition of 2-Diazopropane to Coumarin, The Synthesis-of Derivatives of /1/Benzopyrano/4,3-c/Pyrazol-4(3H)- one and /1/Benzopyrano/3,4-c/Pyrazol-4 (1-H)-one" HETERO-CYCLES, vol. 26, No. 9, 1987, pp. 2425-2431.

Markus E. Scheller and Bruno Frei "Photochemistry of Acylsilanes: Photolysis and Thermolysis of Cyclopropyl Silyl Ketones" Helvetica Chimica Acta, vol. 73, No. 4, 1990, pp. 922-931.

Andre B. Charette, Helene Juteau, Helene Lebel, and Carmela Molinaro "Enantioselective Cyclopropanation of Allylic Alcohols with Dioxaborolane Ligands: Scope and Synthetic Applications" Journal of the American Chemical Society, vol. 120, No. 46, 1998, pp. 11943-11952.

Turin, From Chemical Senses, 1996, vol. 21, No. 6, p. 773-791 Note: The attached reference p. 1-35, which correspond to the above p. 773-791.

Office Action dated May 2, 2007, for U.S. Appl. No. 10/868,489.

Office Action dated Jun. 13, 2007 for U.S. Appl. No. 10/869,579.

CITRAL DERIVATIVES

FIELD OF THE INVENTION

The present invention relates generally to the field of flavorings and fragrances. More particularly, the present invention relates to citral derivatives that provide beverages and other food products, as well as perfumes and other fragrant articles with a lemony scent, while at the same time overcoming the stability limitations of the native citral compound. This application is a continuation of PCT/US02/26446, filed 20 Aug. 2002; which claims priority to U.S. Provisional Application Nos. 60/377,914, filed May 3, 2002; 60/389,298, filed Jun. 17, 2002; 60/355,052, filed Feb. 7, 2002; 60/342,150, filed Dec. 19, 2001, 60/348,580, filed Jan. 15, 2002, PCT/US02/22120, filed Jul. 12, 2002 and PCT/US02/22441, filed Jul. 12, 2002, the contents of each of which are hereby incorporated by reference.

BACKGROUND OF THE INVENTION

Citral (3,7 dimethyl 2,6 octadienal) is a major component of lemon smell, and has the sweet-acidulated character of natural lemon. For largely historical reasons, lemon smell has become associated with freshness and cleanliness, both in drinks and in household products, and in fragrances and flavorings, generally. Lemon drinks, whether natural or synthetic, are naturally acid, which causes rapid degradation of citral to unpleasant-smelling products like cresol. This means that the shelf life of lemonade is correspondingly short, creating an expensive logistical problem. In household products, the problem is of a different nature. In order to associate bacteriological cleanliness with the smell of lemon these products frequently use lemon-scented bleach (hypochlorite). Citral is unstable in bleach, and cannot therefore be used. Instead, its nitrile analogue, geranyl nitrile, with its less satisfactory oily-metallic lemon note has to be used.

The chemical instability of citral is largely due to the two double bonds and an aldehyde group, all of which are potentially susceptible to reaction, particularly when used in harsh environments, such as lemon-scented bleach. It would be desirable to develop citral derivatives with improved useful lifetimes, and, preferably, improved odor intensity, while maintaining the lemon note of citral. The present invention provides such citral derivatives.

SUMMARY OF THE INVENTION

Improved fragrances and flavorings that have a longer useful shelf life than citral are disclosed. In particular, citral derivatives that maintain the fragrance characteristics and lemony flavor of citral, while lowering the allergic properties, providing a longer shelf-life than citral, and/or increasing the odor intensity relative to citral are disclosed. Also disclosed are methods of making the derivatives, and articles of manufacture including the derivatives.

In one embodiment, the citral derivatives are prepared by replacing one or more double bonds in the parent molecule with a cyclopropyl group, which can be unsubstituted, or substituted with one or two lower alkyl, preferably methyl groups. The alkyl groups can optionally be substituted, for example, with electron donating groups, electron withdrawing groups, groups which increase the hydrophilicity or hydrophobocity, and the like. In another embodiment, the derivatives are prepared by replacing one or more aldehyde groups in citral with a nitrile, methyl ether or acetal group. The acetal groups can provide the compounds with a long lasting flavor or fragrance, where the acetals slowly hydrolyze to provide the parent aldehyde compounds. In some embodiments, suitable derivatives are prepared such that the aldehyde and at least one double bond functional group is derivatized as described herein.

Examples of suitable articles of manufacture include candles, air fresheners, perfumes, disinfectant compositions, hypochlorite (bleach) compositions, beverages such as beer and soda, denture cleanser tablets as described, for example, in U.S. Pat. No. 5,571,519, the contents of which are hereby incorporated by reference in their entirety, and flavored orally-delivered products such as lozenges, candies, and the like.

DETAILED DESCRIPTION OF THE INVENTION

Improved citral derivatives, which can be used, for example, as fragrances and flavorings that have a longer useful shelf life than citral, are disclosed. The citral derivatives have a similar odor to citral and also have improved physical and/or chemical properties relative to citral. These improved properties include increased stability to high pH, low pH, improved half-life, lower likelihood of causing allergic reactions, and/or increased odor intensity.

The compounds of Formulas 2-4 described herein have one or more double bonds of citral or the citral derivatives in Formula 1 replaced with a suitable three membered ring. The compounds, and mixtures thereof, are stable in various media in which citral itself is relatively unstable and also have unstable, and also have odor characteristics which are very similar to that of citral. The odor of the compounds of formulas 2-4, or mixtures thereof, possess the same fresh-citrus connotation as citral.

I. Improved Citrals

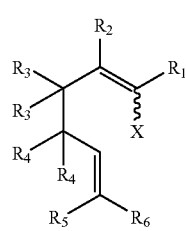

Formula 1

Formula 1 represents citral and citral derivatives that can be modified using the chemistry described herein to replace one or both of the double bonds with appropriate ring structures, thus improving the various physical and/or chemical properties of the molecule. In Formula 1, citral is depicted where X is —C(=O)H, $R_{1-4}$ are H, and $R_5$ and $R_6$ are methyl. However, $R_{1-6}$ can be, independently, H, $C_{1-5}$ alkyl, substituted $C_{1-5}$ alkyl, halo, hydroxy, thiol, thioether, amine, carboxylic acid, ester, nitro, cyano, isocyano, sulfonic acid, urea, and thiourea, where the substituents on the alkyl groups are selected from halo, hydroxy, thiol, thioether, amine, carboxylic acid, ester, nitro, cyano, isocyano, sulfonic acid, urea, thiourea, and the like. X can be —C(=O)H, —OCH$_3$, —C(OR)$_2$H, —CN, —C(=O)CH$_3$, —NC, —C≡C— (alkyne), oxime, C(=O)OR$^7$ (where R$^7$ is a $C_{1-5}$ alkyl), or an oxalate ester, where R is H, $C_{1-5}$ alkyl or $C_{1-5}$ substituted alkyl. The attachment to X shows that the double bond including X can be in the E or Z configuration. In one embodiment, the double bond adjacent to the aldehyde group in citral is saturated (i.e., citronellal), and the derivatives are the same but for the saturated double bond at this position.

Formulas 2-4 below represent citral derivatives as described herein, where one or both of the double bonds are replaced with a suitable three membered ring.

Formula 2

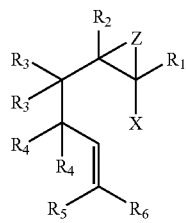

Formula 3

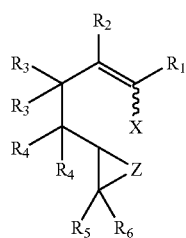

Formula 4

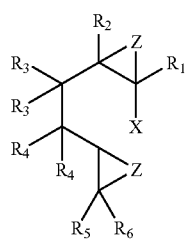

wherein:

Z is O, S, or $C(R)_2$,

R is H, $C_{1-5}$ alkyl, such as methyl, or $C_{1-5}$ substituted alkyl, and

X is —C(=O)H, —$OCH_3$, —$C(OR)_2H$, —CN, —C(=O)$CH_3$, —NC, —C≡C— (alkyne), oxime, C(=O)$OR^7$ (where $R^7$ is a $C_{1-5}$ alkyl), or an oxalate ester, where $R_{1-6}$ are as described above with respect to Formula 1, and in Formula 3, the attachment of the double bond to X indicates that the double bond can exist in the E or Z configuration. The single bond attachments to X, $R^1$, $R^2$, $R^5$ and $R^6$ are not intended to reflect any specific stereochemistry.

In one embodiment of Formulas 2-4, $R_{1-4}$ represent hydrogen, $R_{5-6}$ represent methyl, and Z represents $C(R)_2$. In this embodiment, it is preferred that one or more R groups are methyl, with the other R groups representing hydrogen.

In Formulas 2-4, where the molecule includes two Z groups, one Z can represent saturation at both carbons to which it is bound (i.e., no double bond or cyclopropane, oxirane or thiirane ring), so long as one Z is O, S or $C(R)_2$.

Citral can be cyclopropanated in one or both of the positions, corresponding to the two double bonds of the molecule. Cyclopropanation of the double bond alpha to the carbonyl provides four possible diastereomers, (R,R), (R,S), (S,R) and (S,S). Cyclopropanation of the double bond of the isoprene unit provides two stereoisomers for each of the E and Z isomers of the double bond alpha to the carbonyl, for a total of four isomers. Dicyclopropanation provides eight steriosomeric forms, including all four diastereomers from the cyclopropanation of the double bond alpha to the carbonyl coupled with the R stereoisomer from the cyclopropanation of the double bond in the isoprene unit, and all four diastereomers coupled with the S stereoisomer. The double bond in the isoprene unit of citronnelal can also be cyclopropanated to yield two stereoisomers.

The cyclopropanation reaction can be performed to exhaustion, providing the dicyclopropanated product, or can be performed stepwise, yielding a mixture of mono and dicyclopropanated products. The mono- and di-cyclopropanated products can be separated on the basis of different physical and chemical properties. Diastereomeric forms can be separated on the basis of different properties as well, such as different boiling points and/or crystallization conditions, as is known in the art. Stereoisomers can be isolated using known techniques, such as column chromatography using a chiral solid phase, enzymatic degradation, and reversible formation of diastereomers and separation of the diastereomeric forms, as is known in the art. The presence of the aldehyde functionality permits the rapid and reversible formation of diastereomers by reaction with chiral alcohols to form hemiacetals or acetals, which can be hydrolyzed to reform the aldehyde functionality. Suitable chiral alcohols are well known to those of skill in the art. Accordingly, should it be desired to isolate particular stereoisomers or diastereomers, it would be routine in the art to do so.

While the disclosure is not limited to the following drawing, all sixteen stereoisomeric forms of mono- and di-cyclopropanated citral derivatives, and both stereoisomeric forms of cyclopropanated citronnelal are shown below. The replacement of double bonds with cyclopropane rings in other compounds will likewise often result in the formation of stereoisomers and/or diastereomers, and individual stereoisomers and/or diastereomers can similarly be isolated using conventional separation techniques. Such stereoisomers and/or diastereomers are intended to be within the scope of the invention described herein.

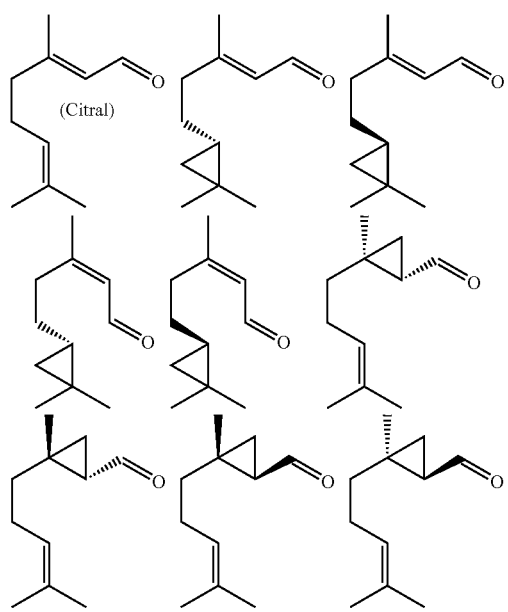

-continued

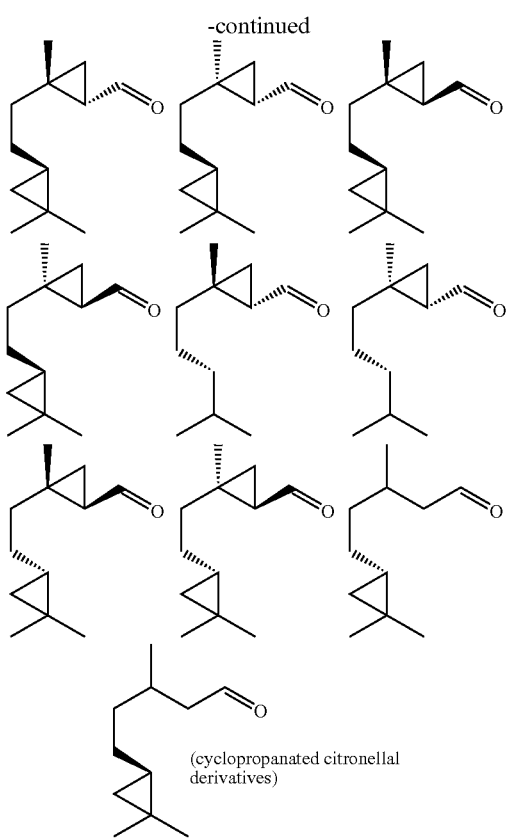

(cyclopropanated citronellal derivatives)

The cyclopropane rings can include a $CH_2$ moiety, or can be substituted with one or two $C_{1-5}$ alkyl (i.e., methyl) groups. The methyl or dimethyl analogues have a tunnelling vibrational spectrum that more closely matches citral than the unsubstituted cyclopropane derivatives, and has a sweeter smell than the unsubstituted cyclopropyl derivatives.

The citral derivatives described herein include derivatives in which one or both of the double bonds is replaced with a (unsubstituted, monoalkyl or dialkyl, where alkyl can be substituted or unsubstituted, and is preferably methyl) cyclopropyl group. The compounds can include, in combination with or in place of a cyclopropyl group, the replacement of the aldehyde with a methyl ether, a nitrile or an acetal group.

II. Methods for Preparing the Citral Derivatives

The citral derivatives of Formulas 2-4 can be prepared using any of the citral derivatives described above in Formula 1, to the extent that the synthetic route is not incompatible with any of the substituents that may be present. In one embodiment, citral (or citronellal) is used as a starting material to prepare various citral (or citronellal) derivatives described in Formulas 2-4 where $R_{1-4}$ are hydrogen and $R_{5-6}$ are methyl.

The synthesis of methyl, dimethyl or unsubstituted cyclopropane derivatives is well known to those of skill in the art, and involves, for example, bromoform reaction to form the dibromocyclopropane derivative, followed by stoichiometric reaction with methyl lithium. The aldehyde group is typically protected as an acetal during the reaction, and deprotected as desired after the reactions take place. In one embodiment, however, the acetals (for example, dimethyl, diethyl, or ethylene glycol) are not deprotected to the aldehyde, such that the flavoring or fragrance includes a portion or entirely the acetals. The acetals can then slowly hydrolyze over time, releasing the lemon scent/flavoring. Alternatively, citral derivatives, including one or two cyclopropane rings, can also include a nitrile or methyl ether group as a replacement for the aldehyde group.

These simple procedures yield derivatives of citral with odor profiles close to citral itself, with greater potency and with far greater acid and bleach stability since the unstable feature, namely the double bond, has been removed.

The same applies to epoxide (OX) and thiirane (TH) rings, shown in the formulas above where Z is O or S. Not counting mixed C=C double bond replacements and stereoisomers, this generates 9 possible molecules from citral alone, all readily accessible in one or two step syntheses from citral itself by processes well known in the art, such as:

Cyclopropanyl replacement: Simmons-Smith cyclopropanation of the aldehyde or corresponding alcohol, followed by periodinane oxidation for the latter to give the aldehyde[1]
[1] Vogel's textbook of practical organic chemistry 5th edition (1989) pp 1106-1108

Oxiranyl replacement: m-chloroperbenzoic acid epoxidation[2]
[2] Ibid, pp 1127-1129

Thiiranyl replacement: bromination of double bond on Amberlite, followed by S'—substitution in sodium sulfides[3]
[3] Choi, J. et al. (1995) Bull. Korean. Chem. Soc., 16, 189-190 Convenient Synthesis of Symmetrical Sulfides from Alkyl Halides and Epoxides Aldehyde Replacement with Nitrile The replacement of aldehyde with nitrile is well known in the art, and described, for example, in U.S. Pat. No. 5,892,092. The '092 patent teaches a process for forming nitrites from aldehydes. Citral derivatives can further be prepared in which one or more a double bonds are converted to (unsubstituted, methyl or dimethyl) cyclopropyl derivatives that also include a nitrile group in place of the aldehyde using the chemistry described above.

III. Articles of Manufacture Including the Citral Derivatives

The citral derivatives can be included in virtually any article of manufacture that can include citral, or for that matter, other lemon fragrances, whether natural or artificial. Examples include bleach, detergents, flavorings and fragrances, beverages, including alcoholic beverages, and the like. The citral derivatives can be used in applications like soaps, shampoos, body deodorants and antiperspirants, solid or liquid detergents for treating textiles, fabric softeners, detergent compositions and/or all-purpose cleaners for cleaning dishes or various surfaces, for both household and industrial use. Of course, the use of the compounds is not limited to the above-mentioned products, as they be used in other current uses in perfumery, namely the perfuming of soaps and shower gels, hygiene or hair-care products, as well as of body deodorants, air fresheners and cosmetic preparations, and even in fine perfumery, namely in perfumes and colognes. These uses are described in more detail below.

Perfume Compositions

The compounds can be used as perfuming ingredients, as single compounds or as mixture thereof, preferably at a range of at least about 30% by weight of the perfume composition, more preferably at a range of at least about 60% by weight of the composition. The compounds can even be used in their pure state or as mixtures, without added components. The olfactive characteristics of the individual compounds are also present in mixtures thereof, and mixtures of these compounds can be used as perfuming ingredients. This may be particularly advantageous where separation and/or purification steps can be avoided by using compound mixtures.

In all cited applications, the citral derivatives can be used alone or in admixture with other perfuming ingredients, solvents or adjuvants of current use in the art. The nature and the variety of these co-ingredients do not require a more detailed description here, which, moreover, would not be exhaustive, and the person skilled in the art will be able to choose the latter through its general knowledge and as a function of the nature of the product to be perfumed and of the desired olfactive effect.

These perfuming ingredients typically belong to chemical classes as varied as alcohols, aldehydes, ketones, esters, ethers, acetates, nitrites, terpene hydrocarbons, sulfur- and nitrogen-containing heterocyclic compounds, as well as essential oils of natural or synthetic origin. A large number of these ingredients described in reference textbooks such as the book of S. Arctander, Perfume and Flavor Chemicals, 1969, Montclair, N.J., USA, the contents of which are hereby incorporated by reference in its entirety, or its more recent versions, or in other works of similar nature.

The proportions in which the citral derivatives can be incorporated in the various products vary within a large range of values. These values depend on the nature of the article or product that one desires to perfume and the odor effect searched for, as well as on the nature of the co-ingredients in a given composition when the compounds are used in admixture with perfuming co-ingredients, solvents or adjuvants of current use in the art.

As an example, the citral derivatives are typically present at concentrations between about 0.1 and about 10%, or even more, by weight of these compounds relative to the weight of the perfuming composition in which they are incorporated. Far lower concentrations than those mentioned above can be used when the compounds are directly applied for perfuming the various consumer products cited beforehand.

The compounds are relatively stable in typically aggressive media for perfumes. Accordingly, they can be used in detergents containing bleaching agents and activators such as, for example, tetraacetylethylenediamine (TAED), hypohalites, in particular hypochlorite, peroxygenated bleaching agents such as, for example, perborates, etc. The compounds can also be used in body deodorants and antiperspirants, for example, those containing aluminum salts. These embodiments are described in more detail below.

Conventional Detergent Ingredients

In addition to the derivatives described herein, the compositions herein include a detersive surfactant and optionally, one or more additional detergent ingredients, including materials for assisting or enhancing cleaning performance, treatment of the substrate to be cleaned, or to modify the aesthetics of the detergent composition (e.g., perfumes, colorants, dyes, etc.). The following are illustrative examples of detersive surfactants and other detergent ingredients.

Detersive Surfactants Non-limiting examples of synthetic detersive surfactants useful herein typically at levels from about 0.5% to about 90%, by weight, include the conventional $C_{11-18}$ alkyl benzene sulfonates ("LAS") and primary, branch-chain and random $C_{10-20}$ alkyl sulfates ("AS"), the $C_{10-18}$ secondary (2,3) alkyl sulfates of the formula $CH_3(CH_2)_x(CH(CH_3)OSO_3^-M^+)$ and $CH_3(CH_2)_y(CH(CH_2CH_3)OSO_3^-M^+)$ wherein x and y are integers and wherein each of x and (y+1) is least about 7, preferably at least about 9, and M is a water-solubilizing cation, especially sodium, unsaturated sulfates such as oleyl sulfate, the $C_{10-18}$ alkyl alkoxy sulfates ("AEx S"; especially EO 1-7 ethoxy sulfates), $C_{10-18}$ alkyl alkoxy carboxylates (especially the EO 1-5 ethoxycarboxylates), the $C_{10-18}$ glycerol ethers, the $C_{10-18}$ alkyl polyglycosides and their corresponding sulfated polyglycosides, and $C_{12-18}$ alpha-sulfonated fatty acid esters. If desired, the conventional nonionic and amphoteric surfactants such as the $C_{12-18}$ alkyl ethoxylates ("AE") including the so-called narrow peaked alkyl ethoxylates and $C_{6-12}$ alkyl phenol alkoxylates (especially ethoxylates and mixed ethoxy/propoxylates), $C_{12-18}$ betaines and sulfobetaines ("sultaines"), $C_{10-18}$ amine oxides, and the like, can also be included in the overall compositions. The $C_{10-18}$ N-alkyl polyhydroxy fatty acid amides can also be used. Typical examples include the $C_{12-18}$ N-methylglucamides. See WO 9,206,154. Other sugar-derived surfactants include the N-alkoxy polyhydroxy fatty acid amides, such as $C_{10-18}$ N-(3-methoxypropyl) glucamide. The N-propyl through N-hexyl $C_{12-18}$ glucamides can be used for low sudsing. $C_{10-20}$ conventional soaps may also be used, however synthetic detergents are preferred. If high sudsing is desired, the branched-chain $C_{10-16}$ soaps may be used. Mixtures of anionic and nonionic surfactants are especially useful. Other conventional useful surfactants are listed in standard texts. See also U.S. Pat. No. 3,664,961 to Norris.

Preferred compositions incorporating only synthetic detergents have a detergent level of from about 0.5% to 50%. Compositions containing soap preferably comprise from about 10% to about 90% soap.

Although the detergent compositions herein can only only detersive surfactants and the citral derivative(s), the compositions preferably contain other ingredients commonly used in detergent products.

Builders

Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic or detergent builders include, but are not limited to phosphate builders such as, the alkali metal, ammonium and allanolammonium salts of polyphosphates (exemplified by the tripolyphosphates, pyrophosphates, and glassy polymeric meta-phosphates), phosphonates, and phytic acid, and non-phosphorous builders such as silicates, carbonates (including bicarbonates and sesquicarbonates), sulphates, and aluminosilicates. Non-phosphate builders are required in some locales.

Organic builders suitable for use herein include polycarboxylate builders such as disclosed in U.S. Pat. No. 3,308,067 to Diehl; U.S. Pat. No. 4,144,226 to Crutchfield and U.S. Pat. No. 4,246,495 to Crutchfield.

Soil Release Agents

Soil Release agents are desirably used in laundry detergents of the instant invention. Suitable soil release agents include those of U.S. Pat. No. 4,968,451 to Scheibel and Gosselink: such ester oligomers can be prepared by (a) ethoxylating allyl alcohol, (b) reacting the product of (a)

with dimethyl terephthalate ("DMT") and 1,2-propylene glycol ("PG") in a two-stage transesterification/oligomerization procedure and (c) reacting the product of (b) with sodium metabisulfite in water; the nonionic end-capped 1,2-propylene/polyoxyethylene terephthalate polyesters of U.S. Pat. No. 4,711,730 to Gosselink et al, for example those produced by transesterification/oligomerization of poly(ethyleneglycol) methyl ether, DMT, PG and poly(ethyleneglycol) ("PEG"); the partly- and fully-anionic-end-apped oligomeric esters of U.S. Pat. No. 4,721,580 to Gosselink, such as oligomers from ethylene glycol ("EG"), PG, DMT and Na-3,6-dioxa-8-hydroxyoctanesulfonate; the nonionic-capped block polyester oligomeric compounds of U.S. Pat. No. 4,702,857 to Gosselink, for example produced from DMT, Me-capped PEG and EG and/or PG, or a combination of DMT, EG and/or PG, Me-capped PEG and Na-dimethyl-5-sulfoisophthalate; and the anionic, especially sulfoaroyl, end-capped terephthalate esters of U.S. Pat. No. 4,877,896 to Maldonado, Gosselink et al, the latter being typical of SRA's useful in both laundry and fabric conditioning products, an example being an ester composition made from m-sulfobenzoic acid monosodium salt, PG and DMT optionally but preferably further comprising added PEG, e.g., PEG 3400. Another preferred soil release agent is a sulfonated end-capped type described in U.S. Pat. No. 5,415,807.

Other Optional Ingredients

The compositions herein can contain other ingredients such as enzymes, bleaches, fabric softening agents, dye transfer inhibitors, suds suppressors, and chelating agents, all well known within the art.

For purposes of defining detergent compositions of the present invention, the pH of the detergent composition is that which is measured at 1% concentration of the detergent composition in distilled-water at 20° C. The detergent compositions herein have a pH of from about 7.1 to about 13, more typically from about 7.5 to about 9.5 for liquid detergents and from about 8 to about 12 for granular detergents.

Formulation with Detergents With or Without Conventional Perfumery Materials

While the derivatives described herein can be used alone and simply mixed with essential detergent ingredient, most notably surfactant, they can also be desirably combined into three-part formulations which combine (a) a non-fragranced detergent base comprising one or more synthetic detergents and (b) one or more of the derivatives described herein. In one embodiment, both aldehydes and acetals are present, such that the aldehydes provide desirable in-package and in-use (wash-time) fragrance, while the acetals provide a long-term fragrance to the laundered textile fabrics.

In formulating the present detergents, the fully-formulated fragrance can be prepared using numerous known odorant ingredients of natural or synthetic origin. The range of the natural raw substances can embrace not only readily-volatile, but also moderately-volatile and slightly-volatile components and that of the synthetics can include representatives from practically all classes of fragrant substances, as will be evident from the following illustrative compilation: natural products, such as tree moss absolute, basil oil, citrus fruit oils (such as bergamot oil, mandarin oil, etc.), mastix absolute, myrtle oil, palmarosa oil, patchouli oil, petitgrain oil Paraguay, wormwood oil, alcohols, such as famesol, geraniol, linalool, nerol, phenylethyl alcohol, rhodinol, cinnamic alcohol, aldehydes, such as citral, Helional™, alpha-hexyl-cinnamaldehyde, hydroxycitronellal, Lilial™ (p-t-butyl-alpha-methyldihydrocinnamaldehyde), methylaonylacetaldehyde, ketones, such as allylionone, alpha-ionone, beta-ionone, isoraldein (isomethyl-alpha-ionone), methylionone, esters, such as allyl phenoxyacetate, benzyl salicylate, cinnamyl propionate, citronellyl acetate, citronellyl ethoxolate, decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, etc., lactones, such as gamma-undecalactone, various components often used in perfumery, such as musk ketone, indole, p-menthane-8-thiol-3-one, and methyl-eugenol. Likewise, any conventional fragrant acetal or ketal known in the art can be added to the present composition as an optional component of the conventionally formulated perfume (c). Such conventional fragrant acetals and ketals include the well-known methyl and ethyl acetals and ketals, as well as acetals or ketals based on benzaldehyde, those comprising phenylethyl moieties, or more recently developed specialties such as those described in a United States Patent entitled "Acetals and Ketals of Oxo-Tetralins and Oxo-Indanes, see U.S. Pat. No. 5,084,440. Of course, other recent synthetic specialties can be included in the perfume compositions for fully-formulated detergents. These include the enol ethers of alkyl-substituted oxo-tetralins and oxo-indanes as described in U.S. Pat. No. 5,332,725; or Schiff Bases as described in U.S. Pat. No. 5,264,615. It is preferred that the pro-fragrant material be added separately from the conventional fragrances to the detergent compositions of the invention.

Formulation with Other Special-Purpose Fragrance Delivering Compounds

Detergents including the derivatives described herein may further, optionally, if desired, contain other known compounds having the capability to enhance substantivity of a fragrance. Such compounds include, but are not limited to, the aluminium alkoxides such as isobutylaluminium diferanylate as disclosed in U.S. Pat. No. 4,055,634; or the known titanate and zirconate esters or oligoesters of fragrant materials such as those disclosed in U.S. Pat. No. 3,947,574, and U.S. Pat. No. 3,779,932, the contents of each of which are hereby incorporated by reference in their entirey. When using such organoaluminum, organotitanium or organozinc derivatives, they may be incorporated into the present formulations at their art-known levels.

Beverage Compositions

The citral derivatives described herein can be incorporated into beverages and impart various flavorings to the beverages. The beverage composition can be a cola beverage composition, and can also be coffee, tea, dairy beverage, fruit juice drink, orange drink, lemon-lime drink, beer, malt beverages, or other flavored beverage. The beverages can be in liquid or powdered form.

The beverage compositions can also include one or more flavoring agents; artificial colorants; vitamin additives; preservatives; caffeine additives; water; acidulants; thickeners; buffering agents; emulsifiers; and or fruit juice concentrates.

Artificial colorants which may be used include caramel color, yellow 6 and yellow 5. Useful vitamin additives include vitamin B2, vitamin B6, vitamin B12, vitamin C (ascorbic acid), niacin, pantothenic acid, biotin and folic acid. Suitable preservatives include sodium or potassium benzoate. Salts which may be used include sodium, potassium and magnesium chloride. Exemplary emulsifiers are gum arabic and purity gum, and a useful thickener is pectin. Suitable acidulants include citric, phosphoric and malic acid, and potential buffering agents include sodium and potassium citrate.

In one embodiment, the beverage is a carbonated cola beverage. The pH is generally about 2.8 and the following ingredients can be used to make the syrup for these compositions: Flavor Concentrate, including one or more of the derivatives described herein (22.22 ml), 80% Phosphoric Acid (5.55 g), Citric Acid (0.267 g), Caffeine (1.24 g), artificial sweetener, sugar or corn syrup (to taste, depending on the actual sweetener) and Potassium Citrate (4.07 g). The beverage composition can be prepared, for example, by mixing the foregoing syrup with carbonated water in a proportion of 50 ml syrup to 250 ml of carbonated water.

In another embodiment, the beverage is a beer or malt beverage. Preferred flavorings for beer and malt beverages include lemon, lime and lemon-lime. Advantageously, the flavorings include citral derivatives in which one of both of the double bonds are replaced with a cyclopropane group, where the cyclopropane groups can, independently, be unsubstituted, or include one or two alkyl or substituted alkyl groups, preferably methyl groups. The amount of flavoring can be adjusted according to taste.

Orally-Delivered Products

Flavored food and pharmaceutical compositions including one or more of the derivatives described herein can also be prepared. The derivatives can be incorporated into conventional foodstuffs using techniques well known to those of skill in the art. Alternatively, the derivatives can be incorporated within polymeric particles, which can, in turn, be dispersed within and/or over a surface of an orally-deliverable matrix material, which is usually a solid or semi-solid substrate. When used in chewable compositions, the derivatives can be released into the orally-deliverable polymeric matrix material as the composition is chewed and held in the mouth, thus prolonging the flavor of the composition. In the case of dried powders and mixes, the flavor can be made available as the product is consumed or be released into the matrix material as the composition is further processed. When two flavors are combined with the polymeric particles, the relative amounts of the additives can be selected to provide simultaneous release and exhaustion of the compounds.

In one embodiment, the flavored composition includes an orally-deliverable matrix material; a plurality of water insoluble polymeric particles dispersed in the orally-deliverable matrix material, where the polymeric particles individually define networks of internal pores and are non-degradable in the digestive tract; and one or more derivatives as described herein entrapped within the internal pore networks. The derivatives are released as the matrix is chewed, dissolved in the mouth, or undergoes further processing selected from the group consisting of liquid addition, dry blending, stirring, mixing, heating, baking, and cooking. The orally-deliverable matrix material can be selected from the group consisting of gums, latex materials, crystallized sugars, amorphous sugars, fondants, nougats, jams, jellies, pastes, powders, dry blends, dehydrated food mixes, baked goods, batters, doughs, tablets, and lozenges.

Chewing Gum

A flavorless gum base can be combined with a citral or other suitable derivative as described herein to a desired flavor concentration. Typically, a blade mixer is heated to about 110F, the gum base is preheated so that it is softened, and the gum base is then added to the mixer and allowed to mix for approximately 30 seconds. The flavored derivative is then added to the mixer and mixed for a suitable amount of time. The gum can be then removed from the mixer and rolled to stick thickness on waxed paper while warm.

Time Release Formulations

In one embodiment, the derivatives described herein are incorporated into a system which can release a fragrance in a controlled manner. These include substrates such as air fresheners, laundry detergents, fabric softeners, deodorants, lotions, and other household items. The fragrances are generally one or more derivatives of essential oils as described herein, each present in different quantities. U.S. Pat. No. 4,587,129, the contents of which are hereby incorporated by reference in their entirety, describes a method for preparing gel articles which contain up to 90% by weight of fragrance or perfume oils. The gels are prepared from a polymer having a hydroxy (lower alkoxy) 2-alkeneoate, a hydroxy (lower alkoxy) lower alkyl 2-alkeneoate, or a hydroxy poly (lower alkoxy) lower alkyl 2-alkeneoate and a polyethylenically unsaturated crosslinking agent. These materials have continuous slow release properties, i.e., they release the fragrance component continuously over a long period of time. Advantageously, all or a portion of those derivatives that include an aldehyde group can be modified to include an acetal group, which can cause the formulations to release fragrance over a period of time as the acetal hydrolyzes to form the aldehyde compound.

The invention will now be illustrated with reference to the following non-limiting example.

EXAMPLE 1

Preparation and Flavor Characteristics of a Cyclopropanated Citral Derivative

Cyclopropanation of Citral to Produce Citral-6,7-Cyclopropane.

The following experimental was based on a well-known method for cyclopropanating olefins, and was conducted numerous times with various stoichiometric equivalents of the cyclopropanation reagents. Optimum results for synthesizing the above-identified mono-cyclopropanated citral derivative were obtained using the amounts shown below. Attempts to increase relative amounts of reagents resulted in the formation of a significant amount of side products. However, this reaction has not been optimized. The use of less than a stoichiometric amount of the diethylzinc and diiodomethane reactants might be advisable if the separation of citral and citral-6,7-cyclopropane were optimized. However, since the separation was not optimized, the cyclopropanation reaction was allowed to proceed to completion. The reactions were conducted behind a blast shield due to the reported possible explosive nature of these reactions. It is believed that cyclopropanations using these reaction conditions may be problematic if the diiodomethane is added too quickly to the reaction mixture Citral-6,7-cyclopropane To an oven dried 500 mL round bottomed flask was added 1,2-dichloroethane (85 mL) under a nitrogen atmosphere. Diethylzinc (30 mL, 1M in hexanes) was added, and then diiodomethane (15 g) was introduced dropwise over 1 hour. Following stirring for 30 mins (a white precipitate formed) citral (1.1 g) was added and the reaction was stirred overnight at room temperature.

The reaction mixture was poured into a potassium carbonate solution (100 mL, 20%) and then filtered through a pad of Celite® in a sintered funnel. The organic layer was separated and dried over sodium sulfate. Filtration of the drying agent, concentration and flash column chromatography with dichloromethane as eluant gave the title compound.

The compound was tasted by two experienced flavorists, who both declared it lemony.

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

I claim:

1. Citral derivatives having one of the following formulas:

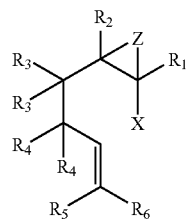

Formula I

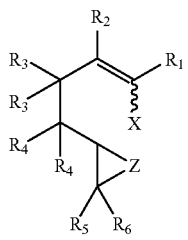

Formula II

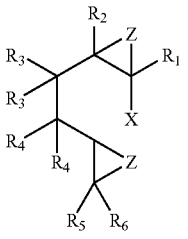

Formula III wherein $R_{1-6}$ are, independently, selected from the group consisting of H, $C_{1-5}$ alkyl, substituted $C_{1-5}$ alkyl, halo, hydroxy, thiol, thioether, amine, carboxylic acid, ester, nitro, cyano, isocyano, sulfonic acid, urea and thiourea, Z is S or saturation at the two carbons to which it is bound, provided that at least one Z is S, X is —C(=O)H, —OCH$_3$, —C(OR)$_2$H, —CN, —C(=O)CH$_3$, —NC, —C≡C—R (alkyne), oxime, C(=O)OR$^7$ (where R$^7$ is a $C_{1-5}$ alkyl), or an oxalate ester, where R is H, $C_{1-5}$ alkyl or $C_{1-5}$ substituted alkyl, wherein the substituents on the substituted alkyl groups are selected from the group consisting of halo, hydroxy, thiol, thioether, amine, carboxylic acid, ester, nitro, cyano, isocyano, sulfonic acid, urea, and thiourea, and wherein the double bond attached to X can be in the E or Z configuration.

2. The citral derivatives of claim 1, wherein X is a nitrile, methyl ether or acetal group.

3. The citral derivatives of claim 1, wherein X is —C(=O)H.

4. The citral derivatives of claim 1, wherein $R_{1-4}$ are hydrogen.

5. The citral derivatives of claim 1, wherein $R_{5-6}$ are methyl.

6. The citral derivatives of claim 1 having the Formula 2, wherein X is —C(=O)H, $R_{1-4}$ are hydrogen and $R_{5-6}$ are methyl.

* * * * *